(12) United States Patent
Malinen et al.

(10) Patent No.: US 8,159,668 B2
(45) Date of Patent: Apr. 17, 2012

(54) SPECTROMETER FOR MEASURING MOVING SAMPLE MATERIAL AND THE METHOD

(75) Inventors: Jouko Malinen, Oulu (FI); Kari Kataja, Oulu (FI); Sini Kivi, Kuopio (FI); Hannu Vasama, Oulu (FI); Reijo Kuusela, Kuopio (FI)

(73) Assignees: Valtion teknillinen tutkimuskeskus, Espoo (FI); Honeywell Oy, Kuopio (FI)

( * ) Notice: Subject to any disclaimer, the term of this patent is extended or adjusted under 35 U.S.C. 154(b) by 176 days.

(21) Appl. No.: 12/676,984

(22) PCT Filed: Sep. 3, 2008

(86) PCT No.: PCT/FI2008/050484
§ 371 (c)(1),
(2), (4) Date: May 5, 2010

(87) PCT Pub. No.: WO2009/030812
PCT Pub. Date: Mar. 12, 2009

(65) Prior Publication Data
US 2010/0284005 A1    Nov. 11, 2010

(30) Foreign Application Priority Data

Sep. 7, 2007    (FI) .................................... 20075622

(51) Int. Cl.
*G01J 3/28* (2006.01)
(52) U.S. Cl. ...................................................... 356/326
(58) Field of Classification Search .................... 356/326
See application file for complete search history.

(56) References Cited

U.S. PATENT DOCUMENTS

| 5,159,404 A | 10/1992 | Bittner |
| 5,166,755 A | 11/1992 | Gat |
| 5,305,887 A | 4/1994 | Krieg et al. |
| 5,422,483 A | 6/1995 | Ando et al. |

(Continued)

FOREIGN PATENT DOCUMENTS

EP    1 498 708 A1    1/2005

(Continued)

OTHER PUBLICATIONS

Finnish Search Report, dated Jun. 30, 2008, from corresponding Finnish application.
International Search Report, dated Feb. 5, 2009, from corresponding PCT application.

*Primary Examiner* — Tarifur Chowdhury
*Assistant Examiner* — Abdullahi Nur
(74) *Attorney, Agent, or Firm* — Young & Thompson

(57) ABSTRACT

An optical or infrared spectrometer is suitable for on-line measurements for industrial, agricultural, field, commercial and other applications. Optical spectrometers are very useful for various analytical measurements. On-line operation is needed for obtaining real-time information, which is useful e.g. for process automation and quality control needs. The invention is based on optical design optimized for measuring moving samples at a distance and includes a light guide for signal homogenization, a linear variable filter for defining multiple measurement wavelengths as well as a linear detector array for detecting optical signals relating to the different wavelengths. There is an element for cooling and stabilizing the operating temperature of both the linear detector array and the linear variable filter, while the spectrometer is operating in variable environmental conditions. Thanks to the optical signal chain designed to maximize the radiance at the detector, the proposed spectrometer can provide high signal-to-noise ratio and high speed.

19 Claims, 3 Drawing Sheets

U.S. PATENT DOCUMENTS

| | | |
|---|---|---|
| 6,313,917 B1 | 11/2001 | Tang et al. |
| 6,420,708 B2 | 7/2002 | Wilks, Jr. et al. |
| 6,505,775 B1 | 1/2003 | Gu et al. |
| 7,428,051 B2 | 9/2008 | Heffels et al. |
| 2001/0055116 A1 | 12/2001 | Maczura et al. |
| 2002/0163641 A1* | 11/2002 | Shroder .................. 356/419 |
| 2002/0191175 A1 | 12/2002 | Coombs et al. |
| 2005/0098713 A1 | 5/2005 | Holland |

FOREIGN PATENT DOCUMENTS

| | | |
|---|---|---|
| WO | 99/40419 A1 | 8/1999 |
| WO | 01/31304 A1 | 5/2001 |
| WO | 2004/013621 A1 | 2/2004 |
| WO | 2007/007165 A2 | 1/2007 |

* cited by examiner

SPECTROMETER FOR MEASURING MOVING SAMPLE MATERIAL AND THE METHOD

TECHNICAL FIELD

The present invention relates to an optical or infrared (IR) spectrometer suitable for on-line measurements for industrial, agriculture, field, commercial and other similar applications. Optical spectrometers are very useful for various analytical measurements. On-line operation is needed for obtaining real-time information, which is useful e.g for process automation and quality control needs.

More specifically the present invention is based on optical design optimized for measuring moving samples at a distance and comprises a light guide for signal homogenisation, a linear variable filter for defining multiple measurement wavelengths as well as a linear detector array for detecting optical signals relating to the different wavelengths.

BACKGROUND ART

After recent developments there are miniature spectrometer modules available, which are based on a fibre optic input connection supplying light to a spectrograph, with optics based on a diffraction grating; and delivering optical signals to a linear detector array for detection. One example of these spectrometer modules is presented in U.S. Pat. No. 5,159,404. Thanks to parallel detection of wavelengths these spectrometers have become popular tools for real time analytical measurements. However, this technology has been limited to shorter wavelengths where suitable, high performance linear detector arrays are available (Si-detectors λ<1100 nm, InGaAs-detectors λ<1600 nm) and where high quality fibre optics is available (quartz λ<2300 nm). On the other hand there is large amount of analytical information available at the longer near infrared (NIR, up to 2500 nm) and IR wavelengths (>2500 nm), which could be exploited for real-time process control and quality monitoring, when high performance and cost effective instrumentation becomes available. Fibre based spectrometer solutions have been proposed for the longer infrared wavelengths, too, but available infrared fibres are expensive and mechanically fragile.

Linear variable filters (LVF) are another method for implementing spectrometers optics, which can provide wavelength separation for linear detector array based spectrometers. U.S. Pat. No. 5,166,755 discloses a spectrometer apparatus comprising image transfer optics, or a lens system, a shutter, an opto-electronic array of photosensitive elements, and a continuous linear variable filter located in overlaying relationship with the array. Line and area arrays are presented as options for the photosensitive array. When exploiting the latter option the two dimensions of the array are called the wavelength axis and the spatial axis, in which case the invention may be used as an imaging radiometer for space applications. Another application of the invention is illuminated by a separate light source aiming for use as a spectroreflectometer. However, this system is not suitable for on-line industrial measurements, which often require monitoring of fast moving non-homogeneous material. In such application various pixels along the wavelength axis would be imaged on different points of the moving sample. This situation would be seen by the user as significantly increased noise in the measured spectra. Furthermore, this invention does not present a solution, where cooled lower noise photosensitive arrays may be used, again very important for high speed on-line applications especially at IR wavelengths.

WO 01/31304 discloses an integrated optics probe for spectral analysis, aiming for applications that require spectral measurements of larger sample areas e.g percentage concentrations of agricultural products as well as colorimeter analysis of samples such as wallpaper. The presented apparatus comprises a polychromatic light source disposed in a first chamber arranged to irradiate a sample with a large illumination spot size, a wavelength separator disposed in a second chamber separating received light of different wavelengths and a detector with a wide viewing aperture, also disposed in the second chamber and positioned to receive light from the wavelength separator for detecting intensities at multiple selected wavelengths. A linear variable filter is proposed for the wavelength separator and a linear detector array for the detecting device. In a preferred embodiment there are separate windows for both the illuminating and the detecting chambers in order to implement a construction, where stray light from the lamp is not received by the detector from within the detection apparatus itself during a sample measurement. Furthermore, a diffuser is proposed in the detecting chamber in the path of the light received from the irradiated sample to ensure that only spectral information is measured without imaging of the sample. This invention is not optimal for on-line measurements requiring high spatial resolution, high measurement speed and simultaneously high signal-to-noise ratio. Illumination of a large area on the sample leads to reduced radiance or brightness on the sample and eventually lower signal-to-noise ratio. There are also high optical losses in the detecting chamber, because only a small portion of the light reflected from the sample enters to the wavelength separation and detection devices. Use of a diffuser would produce further losses in the detected signals, all these features leading to compromised signal-to-noise performance especially when high speed i.e. short integration time is required, which is often the case for on-line measurements serving process automation purposes.

U.S. Pat. No. 6,505,775 discloses a produce data collector with enhanced LVF spectrometer aiming for identifying produce items not labelled with bar codes in connection with a product checkout device. A typical spectrometer according to this invention comprises a linear variable filter splitting incoming light into a number of portions having different wavelengths; a photodetector adjacent the linear variable filter sampling the light portions and producing electrical signals containing information; an optical slit member with a width sufficient to minimize scattering by the interior surfaces of the linear variable filter; and a filter above the optical slit member filtering out light which is outside a wavelength range of operation. This invention has several drawbacks, too, if considered for on-line spectroscopy on a sample web or strip moving at a distance: There are no means for effective homogenisation of the measured radiation, in which case sample movement and distance variations may cause artefacts in the measured spectra. Furthermore there are no means to stabilize the wavelength axis and the measured signal levels against thermally induced variations in the linear variable filter and the linear detector array. Also signal level and signal-to-noise ratio is reduced, because of optical collection losses i.e. illumination radiance present on the sample is not imaged directly on the linear variable filter and the linear detector array.

EP 1 498 708 A1 discloses a small packaged sensor unit for non-destructive inspection of an object for an interior quality (including the ingredients) aiming inspecting fruits, vegetables, plant leaves, fish, meat etc. The sensor unit receives, through an optical fibre bundle, light emitted from an inspection light source and diffuse-transmitted through an inspection object, separates the received light spectroscopically into spectra, and inspects the spectra by an array type sensor for interior quality of the inspection object, wherein a light diffuser, continuous variable interference filter and a photoelectric conversion element are provided after the fibre bundle. Furthermore, fibres in the optical fibre bundle are twisted together to uniformize irregularity in the received light. In the preferred embodiment there is also a light diffuser constituted of optical glass which diffuse-reflects therein the light introduced from the light emitting end of the fibre bundle and emits it on the side opposite towards the continuous variable interference filter. This invention is however not optimal for measurements at a distance i.e. on-line applications, because the light received in the fibre bundle rapidly reduces with increasing measurement distance. On-line applications require that analytical results are not affected by distance variations to the passing sample flow. Furthermore, due to the fibre based design, this sensor is best suitable for shorter wavelengths transmitted by quartz fibres, but less applicable to longer (>2300 nm) wavelengths requiring infrared fibres.

U.S. Pat. No. 6,420,708 B2 discloses a spectroscopy analyzer using a detector array for use in measurements exploiting attenuated total reflection (ATR) technique. A typical implementation of this invention comprises an elongated light source, a sample stage, a device for producing a spectrum and an array of photosensitive elements. In the preferred embodiment an ATR crystal serves as the sample stage and a linear variable filter as the device for producing the spectrum. ATR technique allows measurements at infrared wavelengths too, but it is limited to samples brought to contact with the ATR crystal, e.g. liquid measurements. Therefore this invention is not suitable for on-line measurements at a distance from the passing sample web or strip.

WO 2004/013621 discloses a device for IR-spectrometric analysis of a solid, liquid or gaseus medium. A process probe according to this invention comprises at least one light source, at least one light wave guide connected to a sample, a linearly-variable filter, at least one detector and a regulator/analytical unit. During measurement operation the light is introduced into a defined region of the linearly-variable filter, subsequently the detector is moved into different locations relative to the linearly-variable filter and the regulator/analytical unit determines the spectrum of the medium from the measured values provided by the detector element. According to the principle of operation, this spectrometer records a spectrum in a scanning operation over a period of time. Therefore the spectrometer is not optimal for measurements on fast moving non-homogeneous materials, because different wavelengths are recorded on different points of the sample, which creates "moving-sample noise" in the measured spectra.

The background art summarized above does not meet requirements for typical on-line measurements for process automation applications. It is the purpose of this invention to present a spectrometer solution which

- may be used at a distance from moving sample web or sample transport (on-line), while avoiding artefacts in the spectra due to sample movement and distance variation
- allows good spatial resolution i.e. small measurement area
- allows high measurement speed while maintaining high signal-to-noise ratio
- provides possibility to use thermoelectrically cooled detector arrays for low noise detection
- avoids wavelength limitations of fibre coupled spectrometers
- avoids both signal and wavelength drifts due to variable operating temperature.

SUMMARY OF THE INVENTION

It is an object of the present invention to present a method and apparatus suitable for on-line spectral measurements on moving sample material, which avoids the previous drawbacks.

The method of invention is characterized by illuminating a small area of sample material moving at a distance using broadband optical irradiation, collecting part of the radiation after transmission, scattering or reflection from the sample, receiving the radiation into an input end of a light guide, homogenizing the radiation by multiple reflections inside the light guide, transmitting the radiation from the exit end of the light guide to a sensor module, separating the radiation into different wavelengths using a linear variable filter, converting optical radiation into measurable electrical signals for each wavelength using a linear detector array, processing electrical signals from the pixels into spectral information and finally maintaining the spectral information, comprising of spectral values and wavelengths, stable by cooling and stabilizing the operating temperature of both the linear detector array and the linear variable filter, while the spectrometer is operating in variable environmental conditions.

The apparatus according to the invention is characterized by a broad band light source for delivering irradiance to a small area of sample material moving at a distance, a light guide with an input end and an exit end, receiving back reflected, scattered or transmitted radiation from the sample to the input end and homogenising this radiation spatially to the exit end after multiple reflections inside the light guide, a linear variable filter receiving spatially homogenised radiation from the exit end of the light guide for splitting the broadband radiation into wavelength components, a linear detector array for converting optical radiation into measurable electrical signals, wherein each pixel of the array receives different wavelength components, means for processing electrical signals from the pixels into spectral information and a sensor module containing the linear variable filter, the linear detector array and means for cooling and stabilizing the operating temperature of both the linear detector array and the linear variable filter, while the spectrometer is operating in variable environmental conditions.

In a preferred implementation the linear variable filter is supported in close connection to the linear detector array and both the filter and the detector array are cooled and temperature stabilized inside the sensor package. Linear detector arrays are widely available with integrated cooling devices for optimizing the signal-to-noise performance, and the linear variable filter can be integrated in the temperature controlled volume. For example photoconductive HgCdTe (or MCT or Mercury Cadmium Telluride) arrays may be used as linear detector arrays, and for optimum performance these may be cooled into operating temperatures. The cooling device used in this spectrometer will typically be regulated using feedback from a temperature sensor attached to the detector array. This feedback is fed to a temperature controller and is used to adjust the cooling (or heating) function of the temperature stabilization device. Advantages of these cooling and stabilizing features are discussed in more detail below.

There are also several details, which may be used to improve the performance of the invention. It is preferable that the cross-section of the light guide is rectangular for two reasons: 1) in order to maximize the spatial filtering or homogenizing effect and 2) in order to minimize subsequent coupling losses from the rectangular exit end to the linear detector array, also with a rectangular overall area. Furthermore, at least one dimension in the cross section of the light guide may be designed to reduce towards end of the light guide in order to condense and increase the angular spread of radiation, which may be used to increase signal levels at the linear detector array.

In a further preferred implementation, an optical device can be implemented in between the sample and the light guide for collecting back reflected, scattered or transmitted radiation from the sample at a distance and imaging this radiance into an input end of a light guide. In a similar way another optical device can be implemented in between the light guide and the sensor module for imaging and magnifying the radiance present at the exit end of the light guide into the sensor module. The second optical device is very useful for coupling radiation to a cooled or temperature stabilized detector array, which require an air or vacuum gap for thermal isolation in front of the array, otherwise leading to large optical losses. The spectrometer according to the invention including these optical devices makes it possible to maximize signal at the linear detector array, as will be discussed in more detail below.

In another preferred implementation read out electronics are integrated inside the sensor package. In this case read out electronics includes separate preamplifiers for each pixel as well as multiplexers in order to combine signal outputs from more than one pixel amplifier to one output line, effectively reducing the number of electrical feed troughs from the sensor package. This is practical for producing sensor modules with large number of pixels. Furthermore, integrated read out electronics reduces noise pickup in the amplifier inputs, too.

In another preferred implementation a modulation device, such as a chopper wheel, is implemented in the light source to produce time-modulated irradiance consisting of at least one frequency component and lock-in detection (i.e. phase sensitive detection) means are included in the spectrometer to recover the signal amplitudes present at each pixel of the linear detector array. It is well known, that lock-in detection is very effective to avoid interference from various noise sources including fluorescent illumination, while maintaining close to optimal signal-to-noise performance fore given integration time.

ADVANTAGES OF THE INVENTION

It is an advantage of the invention that radiation from a light source is directed on a small area on the sample, which leads to high irradiance (W/m$^2$) on the sample. After transmission or reflection the sample typically disperses this radiation into hemisphere, which will be seen as radiance (W/m$^2$ sr) by the first optical device in this spectrometer. It is further advantage of this invention that this radiance is imaged sequentially and transmitted (rather than dispersed) eventually to the linear variable filter and the detector array, after only minor transmission and reflection losses have taken place in the first optical device, in the light guide and in the second optical device. Furthermore, the f-number or NA (numerical aperture) of the system at the linear variable filter is maximized to the limit allowed by target resolution (spectral band width). As a conclusion the proposed spectrometer provides very close to maximum signal that can be practically achieved with the chosen light source, the given sample, the chosen detector array and the target spectral resolution. Thanks to the optical signal chain designed to maximize the radiance at the detector, the proposed spectrometer can provide high signal-to-noise ratio and high speed.

It is the second advantage of the system that the light guide after multiple reflections more or less completely homogenizes the line image received form the sample. Therefore the optical radiance present at the exit end of the light guide and thereafter imaged over the linear variable filter are essentially constant over the length of the linear variable filter. This means that any spatial differences in the moving sample are not imaged in the measured spectra. Secondly, also variations in the distance to the moving sample (pass line variations) do not cause artefacts in the measured spectra either. As a conclusion, optical "moving-sample noise" is very effectively minimized.

It is the third advantage of the system that both signal and wavelength axis are temperature stabilized at the sensor module level, while the spectrometer is operating in variable environmental conditions. Wavelength characteristics of all interference filters, including linear variable filters, are drifting certain amount with operating temperature, due to thermal expansion of optical materials and temperature dependence of refractive indices. Integration of the linear variable filter in the temperature stabilized volume avoids this drawback. Furthermore, cooling of the linear variable filter reduces thermal background radiation emitted by the filter, and eventually this reduces thermal background radiation seen by the detector pixels leading to reduced noise in the array and improved signal-to-noise ratio of the spectrometer. In addition to these matters cooling of the detector array optimizes signal-to-noise performance of the array. Furthermore feedback control of the operating temperature maintains a stable temperature at the linear detector array and minimizes any drift in electro-optical response of the pixels. Stabilization of both the signal and wavelength axis is very useful for designing spectrometers for operation in variable environmental conditions. Actually, very few previously known spectrometer techniques can provide a temperature stabilized wavelength scale and wavelength axis.

BRIEF DESCRIPTION OF THE DRAWINGS

FIG. 1 presents a preferred spectrometer according to the present invention. A radiation source 1 and modulating device 2 are shown for producing time-modulated irradiance on a sample 3. Typical implementations may use a halogen lamp as the radiation source and a motor driven chopper wheel designed with blades or holes interrupting the beam sequentially and producing time-modulated irradiance at the modulation frequency, which is optimal for a linear detector array 12 and signal processing electronics 14. Furthermore, there is an optical device 5 for collecting back reflected or transmitted radiation from the actual measurement area 4, within the illuminated area 3 on the sample. Essentially this optical device represents the radiance present on the sample into the input end of an optical light guide 6, therefore minimizing any losses in radiance (analogous to brightness of visible radiation). The optical device 5 may be implemented as a suitable lens or a lens system. More preferably the device 5 can be implemented as a mirror or minor system, because this solution provides possibility to use the same optics over a wide range of wavelengths, if implemented with a proper reflective coating, such as a gold coating. Subsequently the optical signal proceeds through the light guide 6, which serves the purpose of filtering out any features of a spatial image of a sample, which otherwise could produce so called "moving sample" noise in the measured spectra. The radiation proceeding in the light guide is designed to hit the walls multiple times, where it is reflected or refracted depending on the construction of the light guide. The light guide is designed with a rectangular cross section, as discussed previously. The radiance present at the exit end of the light guide is thereafter collected by the second optical device 7, and transmitted out as a magnified image of this radiance on a sensor module 9. At the sensor module the light rays pass a window 10, a linear variable filter 11 and finally the filtered radiation is detected by the various pixels of the linear detector array 12, providing electrical information of the spectrum of the measured sample. The sensor module includes means 13 for cooling and temperature stabilization of the detector array and the linear variable filter. A regulator circuit, such as a PI controller, is also connected to the sensor module as discussed earlier, but not shown in this schematic. For best performance, the magnification of the second optical device 7 is adjusted to illuminate the linear variable filter 11 from within an angular cone limited by a half angle 8. This half angle is typically chosen based on application requirements for spectral resolution and signal-to-noise ratio, because increasing the angle improves signal and signal-to-noise ratio, whereas reducing the angle improves wavelength resolution. Finally, electrical signals detected in the linear detector array are amplified, filtered electrically and digitized in signal processing electronics 14. Read out electronics may be integrated inside the sensor package, but this is not shown in this schematics. It is preferable, that the signal processing includes so called lock-in (phase sensitive) detection as discussed earlier, which outputs the signal amplitudes for each pixel corresponding to the frequency of the time-modulated illumination only.

FIG. 2 aims to clarify optical imaging characteristics of the proposed apparatus by presenting irradiance cross sections at different points in the optical path of the spectrometer. In section A there is a larger area 3 illuminated by the broadband light source. Only part of this area is seen by the first optical device 3, shown as the rectangular area 4. It may be preferable to reduce the size of the irradiance cross section before entering the light guide 6, in order to minimize light guide dimensions. This can be seen in cross section B, which has the same shape but smaller size than cross section A. It is worth to consider that while reducing the area of the cross section, the angular spread of the optical beam will be increased. This is based on the known principles in the radiometry of images, according to which the etendue or throughput Ø is invariant in an optical system and defined as follows:

Figure 1:
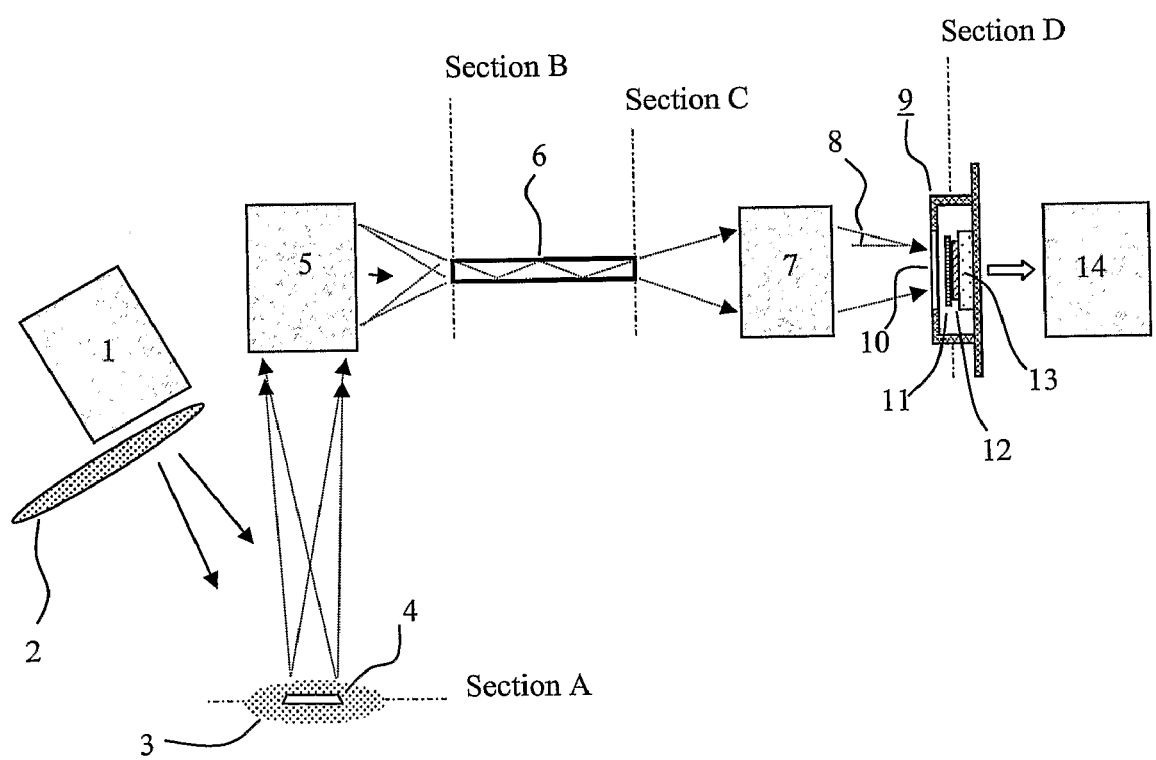
FIG. 1 is schematic illustration of a preferred spectrometer according to the invention
Figure 2:
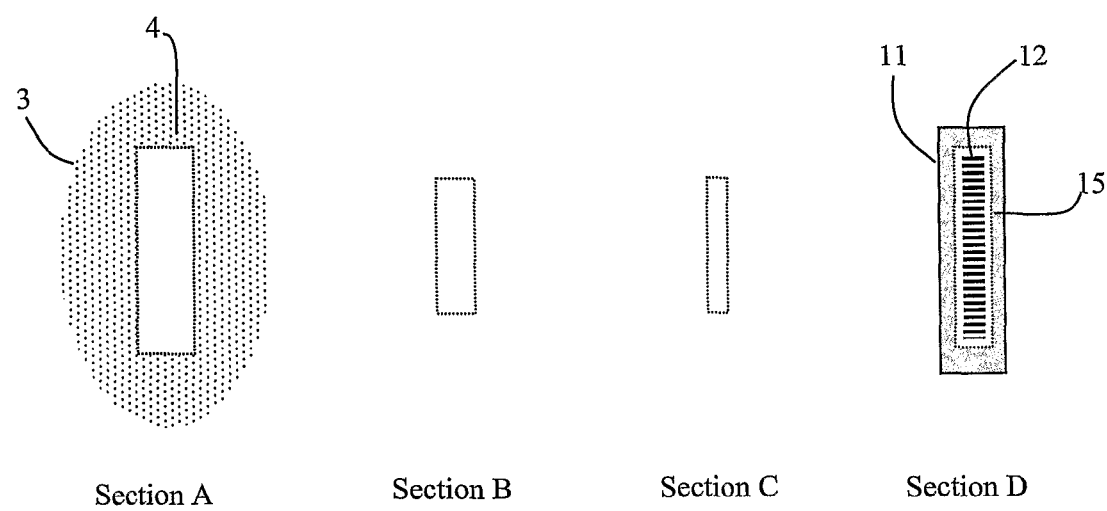
FIG. 2 presents irradiance cross-sections at different points along the optical path

$$\Phi = \Omega_1 \times A_1 = \Omega_2 \times A_2 \qquad (1),$$

where $A_1$ and $A_2$ refer to the areas of two images in an optical system and $\Omega_1$ and $\Omega_2$ are the solid angles of the optical radiation at the same locations. Further down the signal path, section C illustrates a cross section of the irradiance at the exit end the light guide. In the situation shown in FIG. 2 the length of the cross section has remained the same, whereas the width of the cross section is reduced (compared to the previous cross section B). In other words the cross sectional area of the light guide is designed to reduce towards the exit end by gradually altering at least one dimension of the cross section. This is beneficial due to the effect of condensing optical radiation towards the exit end, and subsequently to the linear detector array. With reference to equation 1 it becomes clear, that this spatial condensation effect is accompanied by an increase in ray angles. Therefore this benefit can be realized as long as the maximum angle (8 in FIG. 1) is not exceeded. The final cross section D illustrates the situation at the sensor module, where a linear variable filter 11 can be seen aligned on top of a linear detector array 12. It is advantageous that the radiance image delivered to the sensor is larger than the detector area (in order to fully illuminate all pixels) but smaller than the area of the LVF (in order not to illuminate the edges of the filter possibly producing scattered stray light). According to the present invention, the illumination for section D can be optimized by designing suitable amount of magnification in the second optical device 7.

Figure 3:
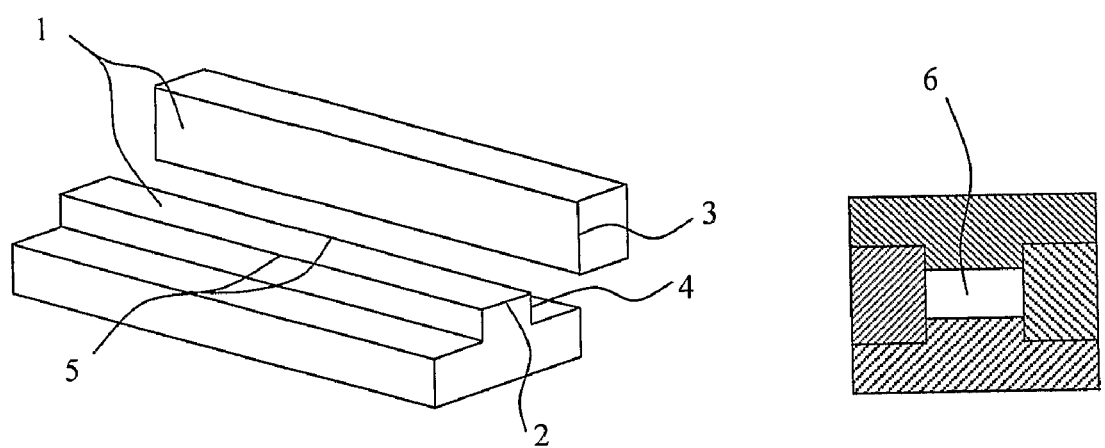
FIG. 3 presents construction of a hollow reflective light guide

FIG. 3 presents an advantageous design of a light guide for use in homogenising infrared radiation. The price of the light guide can be reduced when producing it from metal minor components instead of glass materials which have good transmission properties at IR region such as sapphire. The most important features are the shape accuracy of the light guide and surface roughness at the surfaces 1. The dimensions 2, 3 and 4 fix the shape of the light guide. The importance of the step 4 is to achieve larger area 3 for polishing in order to ease the polishing process. The shape accuracy is easily achieved with precision CNC machining of the substrate. When polishing, only edges 5 along the light guide can suffer rounding. This can also be reduced if this part is polished first (parts can also be off-self minors, metal or glass) and the machined to the correct shape. Finally hollow light guide is manufactured from four different parts as is seen in 6.

What is claimed is:

1. A spectrometer for measuring information from sample material moving at a distance, the spectrometer comprising:
 a) a broad band light source for delivering irradiance to a small area on moving sample material at a distance;
 b) a light guide with an input end and an exit end, receiving back reflected, scattered or transmitted radiation from the sample to the input end and homogenising this radiation spatially to the exit end after multiple reflections inside the light guide;
 c) a linear variable filter receiving spatially homogenised radiation from the exit end of the light guide for splitting the broadband radiation into wavelength components;
 d) a linear detector array for converting optical radiation into measurable electrical signals, wherein each pixel of the array receives different wavelength components;
 e) means for processing electrical signals from the pixels into spectral information; and
 f) a sensor module containing the linear variable filter, the linear detector array and means for cooling and stabilizing the operating temperature of both the linear detector array and the linear variable filter, while the spectrometer is operating in variable environmental conditions.

2. A spectrometer as in claim 1, wherein an optical device is implemented in between the sample and the light guide for collecting back reflected, scattered or transmitted radiation from the sample at a distance and imaging this radiance into an input end of a light guide.

3. A spectrometer as in claim 2, wherein the optical device is implemented as a reflective element or a system of elements.

4. A spectrometer as in claim 1, wherein another optical device is implemented in between the light guide and the sensor module for imaging and magnifying the radiance present at the exit end of the light guide into the sensor module.

5. A spectrometer as in claim 4, wherein the optical device is implemented as a reflective element or a system of elements.

6. A spectrometer as in claim 1, wherein the internal cross-section in the light guide is rectangular.

7. A spectrometer as in claim 6, wherein the shape of the exit end of the light guide is essentially the same as that of the overall light sensitive area of the linear detector array.

8. A spectrometer as in claim 7, wherein another optical device is implemented in between the light guide and the sensor module for imaging and magnifying the radiance present at the exit end of the light guide into the sensor module, and wherein the magnification of the optical device is selected to illuminate the linear detector array completely but not illuminate the edges of the linear variable filter.

9. A spectrometer as in claim 1, wherein the light guide is implemented as a hollow structure consisting of at least two separate parts with the internal surfaces covered using highly reflective material.

10. A spectrometer as in claim 1, wherein at least one dimension of the cross-section in the light guide is reduced towards the exit end in order to condense radiation.

11. A spectrometer as in claim 1, wherein a read out circuit is integrated in the sensor module with separate amplifiers for each pixel and multiplexers connecting several pixels to one output line.

12. A spectrometer as in claim 1, wherein modulation means are implemented in the light source to produce time-modulated irradiance consisting of at least one frequency component and lock-in detection means are included in the spectrometer to recover the signal amplitudes present at each pixel of the linear detector array.

13. A method for measuring spectral information from sample material moving at a distance, the method comprising the steps of:
   a) irradiating a small area on moving sample material at a distance from a broad band light source;
   b) receiving back reflected, scattered or transmitted radiation from the sample to an input end of a light guide, and homogenising this radiation spatially to an exit end after multiple reflections inside the light guide;
   c) receiving spatially homogenised radiation from the exit end of the light guide and splitting the broadband radiation into wavelength components with a linear variable filter;
   d) converting optical radiation into measurable electrical signals in a linear detector array, wherein each pixel of the array receives different wavelength components;
   e) processing electrical signals from the pixels into spectral information; and
   f) maintaining the spectral information, comprising of spectral values and wavelengths, stable by cooling and stabilizing the operating temperature of both the linear detector array and the linear variable filter, while the spectrometer is operating in variable environmental conditions.

14. A method as in claim 13 further comprising the step of collecting back reflected, scattered or transmitted radiation from the sample and imaging this radiance into the input end of the light guide with an optical device implemented in between the sample and the light guide.

15. A method as in claim 13 further comprising the step of imaging and magnifying the radiance present at the exit end of the light guide into the sensor module with another optical device implemented in between the light guide and the sensor module.

16. A method as in claim 15, wherein the magnification of the optical device in claim 15 is selected to illuminate the linear detector array completely but not illuminate the edges of the linear variable filter.

17. A method as in claim 13, wherein the radiation proceeding in the light guide is condensed towards the exit end by reducing at least on dimension of the cross-section compared to the input end.

18. A method as in claim 13, wherein the signals from each pixel are amplified and several of these signals are multiplexed to one output line using read out electronics integrated in the sensor module.

19. A method as in claim 13, wherein the irradiance from the light source is modulated to at least one frequency component and lock-in detection methods are used to recover the signal amplitudes present at each pixel of the linear detector array.

* * * * *